(12) United States Patent
Douglas et al.

(10) Patent No.: US 6,676,950 B2
(45) Date of Patent: Jan. 13, 2004

(54) NEUROKININ RECEPTOR ANTAGONISTS AND METHODS OF USE THEREOF FOR INHIBITING HIV INFECTION

(75) Inventors: Steven D. Douglas, Philadelphia, PA (US); Wen-Zhe Ho, Cherry Hill, NJ (US)

(73) Assignee: The Children's Hospital of Philadelphia, Philadelphia, PA (US)

(*) Notice: Subject to any disclaimer, the term of this patent is extended or adjusted under 35 U.S.C. 154(b) by 0 days.

(21) Appl. No.: 10/077,480

(22) Filed: Feb. 15, 2002

(65) Prior Publication Data

US 2002/0155123 A1 Oct. 24, 2002

Related U.S. Application Data

(60) Provisional application No. 60/316,370, filed on Aug. 31, 2001, provisional application No. 60/268,853, filed on Feb. 15, 2001, and provisional application No. 60/268,850, filed on Feb. 15, 2001.

(51) Int. Cl.$^7$ ............................................... A61K 45/05
(52) U.S. Cl. ........................ 424/278.1; 514/1; 514/317
(58) Field of Search .................... 514/1, 317; 424/278.1

(56) References Cited

U.S. PATENT DOCUMENTS 6,136,824 A * 10/2000 MacLeod et al. ........... 514/317

OTHER PUBLICATIONS

Annunziata et al. "HIV–1 gp120 increases the permeability of rat brain endothelium cultures by a mechanism involving substance P" *AIDS*, vol. 12, No. 18 (Dec. 24, 1998), pp. 2377–2385.*

Cruse et al. *Illustrated Dictionary of Immunology* (Boca Raton, FL, CRC Press, Inc., 1995), p. 309. QR180.4.C78.*

Paul *Fundamental Immunology*, (Philadelphia & New York, Lippincott–Raven Publishers, 1993), pp. 1311–1312 QR181.F84.*

Marriott, I. et al. "Substance P activates NF–κB independent of elevations in intracellular calcium in murine macrophages and dendritic cells"; Journal of Neuroimmunology, 102: 163–171 (2000).

Cioni, C. et al. "Enhanced secretion of substance P by cytokine–stimulated rat brain endothelium cultures"; Journal of Neuroimmunology, 84: 76–85 (1998).

DeGiorgio, R. et al. "Detection of substance P immunoreactivity in human peripheral leukocytes"; Journal of Neuroimmunology, 82: 175–181 (1998).

Ho, W. et al. "Substance P C–terminal octapeptide analogues augment tumor necrosis factor–α release by human blood monocytes and macrophages"; Journal of Neuroimmunology, 82: 126–132 (1998).

Ho, W. et al. "Substance P augments interleukin–10 and tumor necrosis factor–α release by human cord blood monocytes and macrophages"; Journal of Neuroimmunology, 71: 73–80 (1996).

Ho, W. et al. "Human Monocytes and Macrophages Express Substance P and Neurokinin–1 Receptor"; The Journal of Immunology, 159: 5654–5660 (1997).

Toneatto, S. "Evidence of blood–brain barrier alteration and activation in HIV–1 gp120 transgenic mice"; AIDS, 13(17): 2343–2348 (1999).

Kincy–Cain, T. et al. "Substance P–Induced IL–12 Production by Murine Macrophages"; The Journal of Immunology, 158: 2334–2339 (1997).

Lai, J. et al. "Identification of a δ isoform of preprotachykinin mRNA in human mononuclear phagocytes and lymphocytes"; Journal of Neuroimmunology, 91: 121–128 (1998).

Lai, J. et al. "Human lymphocytes express substance P and its receptor"; Journal of Neuroimmunology, 86: 80–86 (1998).

Quinlan, K.L. et al. "Substance P Activates Coincident NF–AT– and NF–κB–Dependent Adhesion Molecule Gene Expression in Microvascular Endothelial Cells Through Intracellular Calcium Mobilization"; The Journal of Immunology, 163: 5656–5665 (1999).

Bae, S. et al. "Autocrine Induction of Substance P mRNA and Peptide in Cultured Normal Human Keratinocytes"; Biochemical and Biophysical Research Communications, 263: 327–333 (1999).

Yi, Y. et al. "Role of CXCR4 in Cell—Cell Fusion and Infection of Monocyte–Derived Macrophages by Primary Human Immunodeficiency Virus Type 1 (HIV–1) Strains: Two Distinct Mechanisms of HIV–1 Dual Tropism"; Journal of Virology, 73(9): 7117–7125 (1999).

Yi, Y. et al. "CXCR–4 Is Expressed by Primary Macrophages and Supports CCR5–Independent Infection by Dual–Topic but Not T–Tropic Isolates of Human Immunodeficiency Virus Type 1"; Journal of Virology, 72(1): 772–777 (1998).

Patterson, B.K. et al. "Regulation of CCR5 and CXCR4 Expression by Type 1 and Type 2 Cytokines: CCR5 Expression Is Downregulated by IL–10 in CD4–Positive Lymphocytes"; Clinical Immunology, 91(3): 254–262 (1999).

(List continued on next page.)

Primary Examiner—Jeffrey Stucker
(74) Attorney, Agent, or Firm—Dann, Dorfman, Herrell and Skillman

(57) ABSTRACT

Compositions and methods are provided which may be used to advantage for the treatment of HIV infection. More specifically, neurokinin receptor antagonists and methods for administration to inhibit HIV invention are disclosed.

15 Claims, 12 Drawing Sheets

OTHER PUBLICATIONS

Annuziata, P. et al. "HIV–1 gp120 increases the permeability of rat brain endothelium cultures by a mechanism involving substance P"; AIDS, 12: 2377–2385 (1998).

Liu, R. et al. "Functional Analysis of the Proximal CCR5 Promoter"; Aids Research and Human Retroviruses, 14 (17): 1509–1519 (1998).

Wahl, S.M. et al. "*Mycobacterium avium* complex augments macrophage HIV–1 production and increases CCR5 expression"; Proc. Natl. Acad. Sci. USA, 95: 12574–12579 (1998).

Huang, Y. et al. "The role of a mutant CCR5 allele in HIV–1 transmission and disease progression"; Nature Medicine, 2(11): 1240–1243 (1996).

Berger, E.A. et al., "A new classification for HIV–1"; Nature, 391: 240 (1998).

Castagliuolo, I. et al. "Neurokinin–1 (NK–1) Receptor Is Required in *Clostridium difficile*–induced Enteritis"; J. Clin. Invest., 101(8): 1547–1550 (1998).

Castagliuolo, I. et al. "Increased substance P responses in dorsal root ganglia and intestinal macrophages during *Clostridium difficile* toxin A enteritis in rats"; Proc. Natl. Acad. Sci. USA, 94: 4788–4793 (1997).

Lucey, D.R. et al. "Characterization of Substance P Binding to Human Monocytes/Macrophages"; Clinical and Diagnostic Laboratory Immunology, 1(3): 330–335 (1994).

Laurenzi, M.A. et al. "The Neuropeptide Substance P Stimulates Production of Interleukin 1 in Human Blood Monocytes: Activated Cells are Preferentially Influenced by the Neuropeptide"; Scan. J. Immunol., 31: 529–533 (1990).

Dickerson, C. et al. "Neuropeptide regulation of proinflammatory cytokine responses"; Journal of Leukocyte Biology, 63: 602–605 (1998).

Lee, H. et al. "Substance P Augments Tumor Necrosis Factor Release in Human Monocyte–Derived Macrophages"; Clinical and Diagnostic Laboratory Immunology, 1(4): 419–423 (1994).

\* cited by examiner

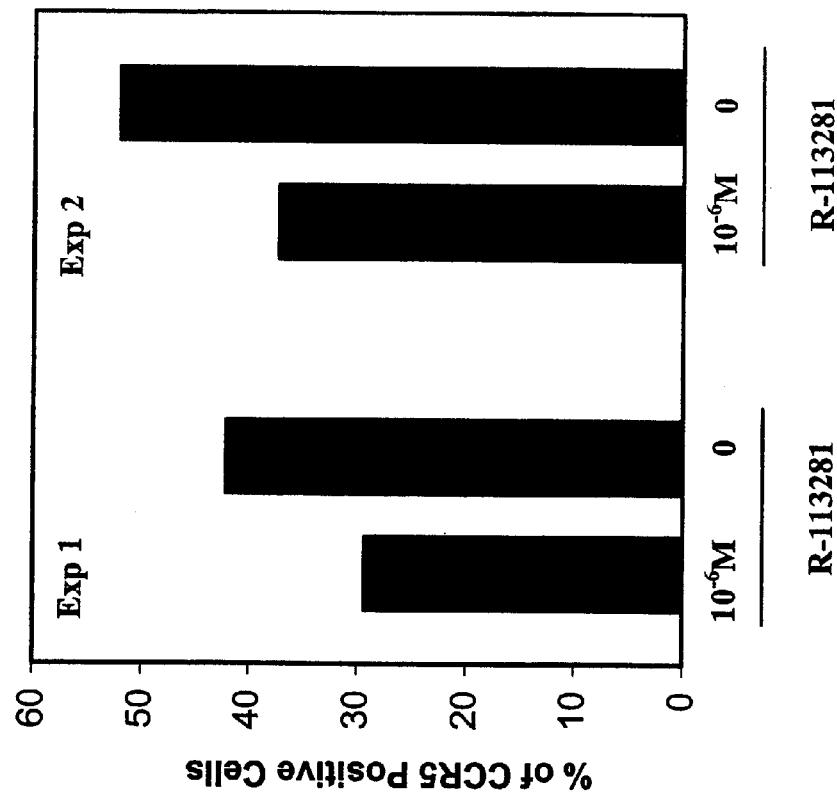
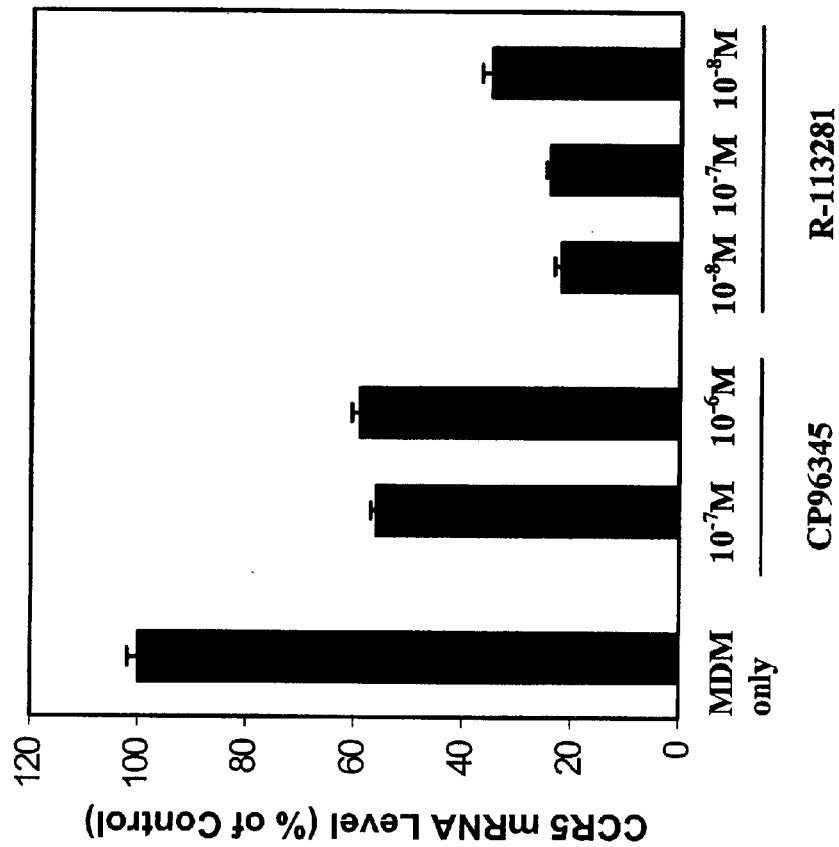
Fig. 15A
Fig. 15B

NEUROKININ RECEPTOR ANTAGONISTS AND METHODS OF USE THEREOF FOR INHIBITING HIV INFECTION

This application claims priority under 35 U.S.C. §119(e) to U.S. Provisional Application Nos. 60/268,850 and 60/268,853, each filed Feb. 15, 2001, and 60/316,370, filed Aug. 31, 2001, the entire disclosures of which are incorporated by reference herein.

Pursuant to 35 U.S.C. Section 202(c), it is acknowledged that the United States Government has certain rights in the invention described herein, which was made in part with funds from the National Institutes of Health Grant Nos. DA12815 and MH49981.

FIELD OF THE INVENTION

The present invention relates to compositions and methods for the treatment of HIV infection. More specifically, the invention provides antagonists that inhibit neuropeptide/neuropeptide receptor interactions and methods of administering such antagonists for the treatment of HIV infection.

BACKGROUND OF THE INVENTION

Several publications are referenced in this application by numerals in parentheses in order to more fully describe the state of the art to which this invention pertains. Full citations for these references are found at the end of the specification. The disclosure of each of these publications is incorporated by reference herein.

The neurokinins are a family of neuropeptides that share a common C-terminal region. The main members are Substance P (SP), neurokinin A and neurokinin B. Neurokinin actions are mediated by at least three distinct receptors, NK1, NK2, and NK3. Members of the neurokinin family of neuropeptides modulate functions of cells that are the primary targets for HIV-1 infection, i.e., human T lymphocytes, monocytes and macrophages through interactions with these NK receptors. Substance P (SP), the most extensively studied and potent member of the neurokinin family, is a modulator of neuroimmunoregulation, and in particular, the immune functions of mononuclear phagocytes. SP specifically activates NF-KB, a transcription factor involved in the control of cytokine expression (1,2) and stimulates human peripheral blood monocytes to produce inflammatory cytokines including interleukin 1 (IL-1), IL-6, IL-12 and tumor necrosis factor alpha (TNF-α) (3–5). These cytokines alter HIV expression in T cells and monocytes in vitro (6,7).

SP also plays a role in autocrine regulation in macrophage function (8,9). For example, in the macrophage cell line, P388D1, anti-SP antibody depletion of macrophage secreted SP from the culture resulted in abrogation of SP-increased IL-1 production (8). SP autocrine regulation in monocyte-derived macrophages (MDM) is further evidenced by the presence of specific cell membrane SP receptors (13) and production of SP protein by macrophages (8, 9, 14–17). SP mRNA and protein are present in monocyte/macrophages (M/M) and lymphocytes isolated from human peripheral blood (16, 18). Neurokinin-1 receptor (NK-1R) has also been identified in these cells. Autocrine regulation by SP has also been suggested in other cell types (10–12).

SP and its receptor, NK-1R, are also involved in the modulation of HIV infection both in vivo and in vitro. Azzari et al. (20) observed that HIV-positive children had higher plasma levels of SP compared to HIV-negative children. Annunziata et al. (21) also showed that SP plays a critical role in HIV gp120-induced increases in permeability of rat brain endothelium cultures. Significant SP immunoreactivity has also been observed in HIV gp120 transgenic mouse brain vessels in comparison to non-transgenic mouse brain vessels, suggesting that SP is involved in HIV gp120-induced changes in the vascular component of the blood-barrier (12).

HIV infection continues to be a global issue. While effective anti-HIV treatments are available, it is clear that a need exists of additional beneficial therapeutic agents for combating this disease.

SUMMARY OF THE INVENTION

In accordance with the present invention, it has been discovered that SP and the NK receptor family are actively involved in the modulation of HIV infection of human cells. Thus, in a first aspect, methods for inhibiting HIV infection in a patient in need thereof comprising the administration of at least one antagonist specific for the NK receptor family in an effective amount to said patient are provided. An exemplary antagonist has specific binding affinity for the NK1 receptor, and includes without limitation, CP-96,345. Other exemplary antagonists are combined antagonists having binding affinity for the NK1, NK2 and NK3 receptors, such as R-113281.

In yet another aspect of the invention, multiple antagonists at NK receptors may be adminstered in combination. An exemplary combination of antagonists for inhibiting HIV infection comprises both CP-96,345 and R-113281.

The antagonists of the invention may be administered by any route which delivers an effective amount of the antagonist for inhibition of HIV infection. Such routes include without limitation, intravenous administration, parenteral administration, topical administration, and oral administration.

In yet another aspect of the invention, the antagonists of the invention are administered in combination with at least one additional anti-retroviral agent. Additionally, administration of the antagonists of the invention may be combined with the administration of an AIDS vaccine.

Finally, methods for inhibiting HIV infection of a monocyte derived macrophage are also disclosed. In a preferred embodiment, such methods comprise contacting said macrophage with at least one NK receptor antagonist in an amount effective to inhibit HIV entry. NK receptor antagonists may be administered alone or in combination with other NK receptor antagonists or in combination with additional anti-retroviral agents.

BRIEF DESCRIPTION OF THE FIGURES

FIGS. 15A and 15B. A pair of graphs showing the effects of NK receptor antagonists on CCR5 expression in MDM. FIG. 15A: MDM were incubated with CP96345 ($10^{-7}$ M to $10^{-6}$ M) or R-113281 ($10^{-8}$ M to $10^{-6}$ M) as indicated for 4 hours. Relative CCR5 mRNA level was quantified by a real-time RT-PCR assay. Untreated MDM was used a control. FIG. 15B: MDM were incubated with or without R113281 ($10^{-6}$ M) for 24 hours. Percentage of CCR5 positive cells were then determined by flow cytometry assay. Two representative experiments are shown.

DETAILED DESCRIPTION OF THE INVENTION

Figure 1A:
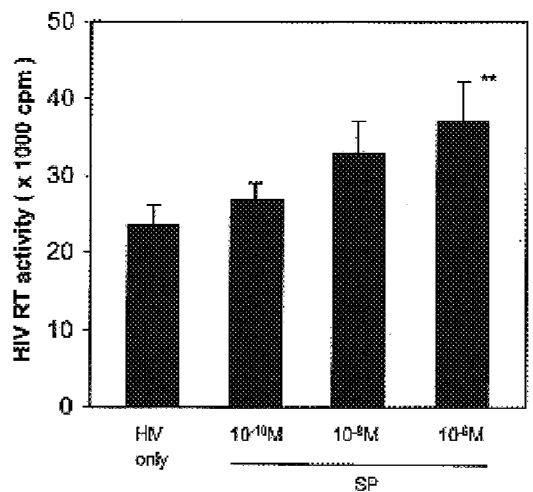
FIGS. 1A and 1B. (1A) SP up-regulated HIV Bal replication in MDM. MDM were incubated with different concentrations of SP as indicated and infected with HIV Bal strain. Untreated and HIV infected MDM were used as an infection control (HIV only). HIV RT activity was determined in triplicates in the culture supernatants 12 days after infection. The data shown are presented as the mean±SD of triplicate cultures and are representative of three experiments (** $P<0.01$, SP $10^{-6}$M vs untreated). (1B) Effect of CP-96,345 on HIV infection of human MDM. The HIV Bal strain was used to infect MDM in the presence or absence of CP-96,345 ($10^{-8}$ to $10^{-6}$ M). HIV RT activity was measured in the supernatants 8 and 12 days after infection. HIV RT activity in CP-96,345-treated and infected MDM culture supernatants were expressed as percentage of that of untreated and HIV-infected MDM controls.

Substance P (SP), a member of the neurokinin family of neuropeptides, is a potent modulator of neuroimmunoregulation. Significantly, SP modulates functions of human T lymphocytes, monocytes and macrophages, the primary target cells for HIV-1 infection. The role that SP and its receptor, neurokinin 1 (NK-1R) play in HIV infection is described herein. SP was found to enhance HIV replication in human blood-isolated mononuclear phagocytes. These data strongly suggest that SP-NK-1R interaction is an important trigger of intracellular events that are involved in modulation of HIV infection of human blood monocyte-derived macrophage (MDM). Based on these results, novel approaches for the treatment of HIV infection have been developed which inhibit HIV infection by targeting the NK receptor interactions on human immune cells to block the virus from entering and killing the cells.

In accordance with the present invention, the present inventors have discovered that neurokinin (NK) receptor antagonists, including tachykinin receptor and neurokinin receptor antagonists, inhibit HIV-1 replication in human blood MDM. Exemplary antagonists include, without limitation, the combined tachykinin receptor antagonist, R-113281 (available from Sankyo Co Ltd, Tokyo, Japan) (See Nishi et al. Bioorganic and Medicinal Chemistry Letters 10:1665–1668 (2000)) and the SP antagonist, CP-96,345 [2S,3S)-cis-2-(diphenylmethyl)-N-[(2-methoxyphenyl)-methyl]-1-azabicyclo [[2.2.2]-octan-3-amine] (Pfizer, Groton Conn.). These antagonists work by blocking the interaction between neuropeptides and their receptors on the surface of MDMs. For example, CP-96,345 interferes with SP and its interaction with NK-1R, whereas the R-113281 combined antagonist interacts with all three neurokinin receptors (NK-1R, NK-2R and NK-3R). Such agents may be used alone or in combination to interrupt the process by which HIV enters macrophages through receptors on the macrophages' cell surfaces, thereby blocking HIV infection at an early stage and precluding the virus from avoiding immune detection while in a latent state inside immune cells.

The following description sets forth the general procedures involved in practicing the present invention. To the extent that specific materials are mentioned, it is merely for purposes of illustration and is not intended to limit the invention. Unless otherwise specified, general biochemical and molecular biological procedures, such as those set forth in Sambrook et al., *Molecular Cloning*, Cold Spring Harbor Laboratory (1989) (hereinafter "Sambrook et al.") or Ausubel et al. (eds) *Current Protocols in Molecular Biology*, John Wiley & Sons (1997) (hereinafter "Ausubel et al.") are used.

I. Definitions:

The following definitions are provided to facilitate an understanding of the present invention:

"Neurokinin receptor antagonists" refer to agents which bind the neurokinin receptor(s) to block and/or inhibit receptor function. Exemplary antagonists include CP-96,345 and R-113281.

To "treat" or "inhibit" HIV infection refers to the administration of agents that are effective for diminishing symptoms, decreasing viral load or decreasing viral replication.

An "AIDS vaccine" is an agent which is used to immunize a test subject against HIV infection. Such vaccines are described for example in Belyakov et al. Nat. Med. 7(12): 1320–1326 (2001) and Johnston, MI, AIDS Alert 16(11): 137–141 (2001).

An "anti-retroviral agent" is any agent which inhibits replication or transmission of a retrovirus.

II. Methods of Administration:

The present invention further provides "compositions" in biological compatible solution, pharmaceutically acceptable excipient, carrier, buffer, stabilizer or other materials well known to those skilled in the art, comprising the antagonists of the invention. A biologically compatible solution is a solution in which the antagonists of the invention are maintained in an active form, e.g., in a form able to effect a biological activity. Generally, such a biologically compatible solution will be an aqueous buffer, e.g. Tris, phosphate, or HEPES buffer, containing salt ions. Usually the concentration of salt ions will be similar to physiological levels. Biologically compatible solutions may include stabilizing agents and preservatives.

Such compositions may be formulated for administration by oral, parenteral, intranasal, subcutaneous, and intraocular routes. Parenteral administration is meant to include intravenous injection, intramuscular injection, intraarterial injection or infusion techniques. The compositions may be administered parenterally in dosage unit formulations containing standard well known non-toxic physiologically acceptable carriers, adjuvants and vehicles as desired.

The preferred sterile injectable preparations may be a solution or suspension in a nontoxic parenterally acceptable solvent or diluent. Examples of pharmaceutically acceptable carriers are saline, buffered saline, isotonic saline (e.g.

monosodium or disodium phosphate, sodium, potassium, calcium, or magnesium chloride, or a mixture or such salts), Ringers solution, dextrose, water, sterile water, glycol, ethanol, and combinations thereof. 1,3-butanediol and sterile fixed oils are conveniently employed as solvents or suspending media. Any bland fixed oil may be employed including synthetic mono- or di-glycerides. Fatty acids such as oleic acid also find use in the preparation of injectables.

The present invention provides "methods of treatment" which comprise the administration to a human or other animal of an effective amount of a composition of the invention in order to inhibit HIV infection.

Effective amounts vary, depending on the age, type and severity of the condition to be treated, body weight, desired duration of treatment, method of administration, and other parameters. Effective amounts are determined by a physician or other qualified medical professional.

III. Materials and Methods:

The following materials and methods are provided to facilitate the practice of the present invention:

A. Cells

Peripheral blood was obtained from healthy normal adult donors. The blood samples were identified as HIV-1 antibody negative by anonymous testing with the ELISA method (Coulter Immunology, Hialeah, Fl.). Monocytes were purified according to previously described techniques (23, 24).

ACH-2 and U38 cell lines (25, 26) were obtained from the NIH AIDS Reagent Program. DNA extracted from ACH-2 cells was used as a positive standard for HIV DNA PCR as previously reported (27). The U38 cell line contains stably integrated, silent copies of the HIV LTR (long terminal repeat) promoter linked to a CAT (chloramphenicol acetyltransferase) gene and was used to study the effect of SP and/or CP-96,345 and R-113281 on the activation of HIV LTR promoter.

B. Reagents

Fluorescein (FITC)-conjugated anti-CCR5, anti-CD4, anti-CD14, IgG1, and IgG2 a were obtained from PharMingen (San Diego, Calif.). Anti-CXCR4-FITC was obtained from R&D Systems (Minneapolis, Minn.). SP, a rabbit anti-SP antibody, and lipopolysaccharide (LPS) were obtained from Sigma (St. Louis, Mo.). Sodium azide was removed from the anti-SP antibody using CHROMA SPIN STE-30 Columns (Clonthech, Palo Alto, Calif.). The non-peptide SP antagonist, CP-96,345, and its 2R, 3R inactive enantiomer, CP-96,344 (28), were generously provided by Pfizer Inc. CP-96,345 and CP-96,344 were dissolved in FPLC grade $H_2O$ at the concentration of $10^{-3}M$, filtered through a 0.22 um filter (Millipore Corp. Bedford, Ma.) and stored at $-70°$ C.

C. HIV Strains

Based upon their differential use of the major HIV co-receptors, HIV isolates have been referred to as R5, X4 or R5X4 strains, respectively (29). The M-tropic (macrophage-tropic) R5 prototype strains (Bal and ADA), dual tropic strain (89.6) and X4 primary isolate (UG024), were obtained from the NIH AIDS Reagent Program. Primary M-tropic isolates (BL-6 and CSF-6) were isolated from the blood and cerebrospinal fluid cells, respectively, of a subject with AIDS.

D. Antagonist Treatment and HIV Infection

SP and CP-96,345 treatment: 7-day-cultured macrophages in 24-well plates ($1\times10^6$ cells/well) were incubated with or without CP-96,345 or its inactive enantiomer, CP-96,344, for 2 h before infection with HIV. The cells were also incubated with SP and/or anti-SP antibody. In this case, SP was incubated with (1:1000 dilution in 10% FCS DMEM) or without anti-SP antibody at room temperature for 10 min and then the mixture was added to the cell cultures for 2 h. When the cells were treated with the combination of CP-96,345 and SP, or CP-96,345, SP and anti-SP antibody, CP-96,345 was incubated with the cell culture for 10 min and then SP was added to the MDM or CP-96,345, SP and anti-SP (1:1000 in 10% FCS DMEM) were incubated for 10 min at room temperature and the mixture was incubated with the MDM for 2 h before infection with HIV. Untreated MDM served as controls. The cells were treated prior to, during, and throughout the infection. Experiments using R-113281 or its inactive enantiomer were performed in a similar manner.

HIV Infection: After 2 h incubation with or without the reagents described above, the cells were infected with equal amounts of cell-free HIV based on p24 antigen content (20 $ng/10^6$ cells) overnight, and then washed to remove unbound virus. Fresh media containing SP and/or CP-96,345 or anti-SP antibody were added to the MDM as described above. The culture media and the reagents were replaced twice weekly. The culture supernatants were harvested for HIV reverse transcriptase (RT) activity determinations. After HIV infection, the MDM were incubated for 8 to 12 days. At the termination of the experiments, cellular RNA was extracted for assessment of HIV gag gene expression using RT-PCR or real time RT-PCR assays.

E. HIV RT Assay

The HIV RT activity assay was carried out based on the technique of Willey et al. (30) with modification (22).

Syncytia formation: To study the effect of neuropeptide antagonists on HIV-induced syncytia formation in MDM, 7-day-cultured macrophages were incubated in the presence or absence of CP-96,345 ($10^{-7}M$) for 2 h and then infected with HIV Bal strain. MDM which were neither incubated with CP-96,345 nor infected with HIV were used as a cell culture control. The morphology of HIV-induced syncytia formation was observed and photographed by a light microscopy (X 400) 12 days after HIV infection.

Pseudotype reporter virus entry assay: Recombinant luciferase-encoding HIV virions pseudotyped with Env from the M-tropic ADA (CCR5-dependent) and amphitropic murine leukemia virus (MLV) (CCR5-independent) were used to study HIV infection of MDM incubated with or without CP-96,345 or R-113281. The Env-deleted luciferase reporter plasmid PNL-Luc-E-R+ (kindly provided by N. Landau) was cotransfected into 293T cells along with plasmids encoding the ADA or MLV Env genes as previously described (31). Supernatants were collected 48 h later, assayed for $p24^{Gag}$ antigen content, and frozen at $-80°$ C. MDM ($2.5\times10^5$ cells/well, in 48-well plates) were incubated overnight with or without CP-96,345 or R-113281 and then infected using 20 ng of $p24^{Gag}$ antigen equivalent of each pseudotype HIV per well, in the presence of polybrene (7.5 $\mu g/ml$). At 72 h postinfection, the cells were lysed in 150 $\mu l$ of 0.5% Triton-X-100 in PBS. Lysate (50 $\mu l$) was mixed with an equal volume of luciferase substrate (Promega, Madison, Mich.) and luciferase activity was determined in a microtiter plate luminometer (Dynex Technologies, Chantilly, Va.). The results were expressed as relative light units (RLU) in CP-96,345-treated or R-113281-treated and infected MDM as a percentage of that in untreated and infected MDM.

Chloramphenicol acetyltransferase (CAT) activity assay: U38 cells ($2\times10^6$ cells) were incubated with different concentrations of SP and/or CP-96,345 or R-113281 for 48 h. Untreated U38 cells were used as a background control. Cellular proteins were extracted using 1X Reporter Lysis Bufffer (Promega Corp., Madison, Wis.). The lysates were incubated with a mixture containing 0.15 $\mu$Ci of $^{14}$C-labeled chloramphenicol (DuPont Inc., Boston, Mass.) and 200 $\mu$g/ml of n-Butyryl CoA (Promega Corp., Madison, Wis.) in a total volume of 125 $\mu$l at 37° C. for 3 h. The acetylated forms of chloramphenicol were extracted with xylene (Aldrich Chemical Company, Milwaukee, Wis.). CAT activity of each sample was quantified using a liquid-scintillation counter (Packard Instrument Company, Downers Grove, Ill.). The results were expressed as the ratio of CAT activity (CPM) of the SP and/or CP-96,345-treated or R-113281-treated U38 to that of the background control.

F. Flow Cytometry

In order to determine the expression of CCR5, CD4, CXCR4 and CD14 on CP-96,345-treated monocytes/macrophages, monocytes or MDM (106 cells) were either incubated with or without CP-96,345 or its inactive enantiomer, CP-96,344, at different concentrations for 24 h. The cells were removed from the culture plate and then resuspended in 100 $\mu$l of phosphate-buffered saline (PBS). After incubation with 20 $\mu$l of either anti-CCR5-FITC or anti-CXCR4-FITC or anti-CD4-FITC or anti-CD14-FITC for 45 min at 4° C., the cells were washed twice with PBS and fixed with 1% paraformaldehyde in PBS. Fluorescein-conjugated control antibodies were isotype-matched IgG. Fluorescence was analyzed on an EPICS-Elite flow cytometer (Beckman-Coulter Electronics, Hialeah, Fla.).

G. RNA Isolation

Total RNA was isolated from human peripheral blood MDM ($10^6$ cells) using Tri-Reagent (Molecular Research Center, Cincinnati, Ohio) as we previously reported (16).

Reverse transcription: Total RNA (1 $\mu$g) was reverse transcribed using Reverse Transcription System (Promega, Madison, Wis.) with the specific primers (antisense) for HIV gag (5'-TGACATGCTGTCATC-ATTTCTTC-3'; SEQ ID NO: 1) (27) or CCR5 (5'-CCTGTGCCTCTTCTTCTCATTTCG-3'; SEQ ID NO: 2) (32) for 1 h at 42° C. RT reactions was terminated by incubating the reaction mixture at 99° C. for 5 min and then kept at 4° C. The resulting cDNA was used as a template for PCR amplification or real time PCR quantification.

Polymerase chain reaction (PCR) analysis: PCR amplification of CCR5 and HIV gag cDNA was performed with one tenth of the cDNA for 35 cycles (CCR5) (32) or 40 cycles (gag) (27) using AmpliTaq Gold (Perkin ElmerCetus, Foster City, Calif.) in a GeneAmp PCR System 2400 (Perkin Elmer-Cetus). $\beta$-Actin was used as a control to monitor the amount and integrity of RNA in each sample (Clontech, Palo Alto, Calif.). Real time PCR was performed with one tenth of cDNA using ABI Prism 7700 Sequence Detection System (Perkin Elmer). The reaction mixture contained 0.25 mM of dNTPs, AmpliTaq Gold (1.5 U), 5 mM of $MgCl_2$, 50 pmole of each of the two primers (SK38: 5'-ATAATCCACCTATCCCAGTAGGAGAAAT-3'(SEQ ID NO: 3); SK39: 5'-TTTGGTCCTGTCTTATGTCCAGAATGC-3'; SEQ ID NO: 4), 20 pmole of the molecular beacon probe (SK19: 5'ATCCTGGGGATTAAATAAAATAGTAAGAATGTATA GCCCTAC-3'; SEQ ID NO: 5) labeled with FAM (a fluorophore) at its 5' end and DABCYL (a quencher) at the 3'end. The cycle conditions were 95° C. 10 min followed by 40 cycles of 95° C. 15 sec and 60° C. 1 min. The known amounts of HIV DNA isolated from ACH-2 cells were used as standard controls. All standards and samples were run in duplicates. HIV gag, CCR5, $\beta$-Actin primer pairs and the probe (SK19) were synthesized by Integrated DNA Technologies, Inc. (Coralville, Ind.).

H. CP-96,345 Treatment and Cytokine Production

In order to determine the role of CP-96,345 in the regulation of cytokine secretion, 7-day-cultured MDM were incubated with or without CP-96,345 ($10^{-9}$ to $10^{-7}$M) and/or LPS (1 ng/ml) for 24 h. The culture supernatants were collected to determine TNF-A and IL-6 levels by ELISA. The ELISA kits were purchased from Endogen, Inc. (Woburn, Mass.).

I. Statistical Analysis

The data were analyzed using the Student's t-test for paired samples.

Further details regarding the practice of this invention are set forth in the following examples, which are provided for illustrative purposes only and are in no way intended to limit the invention.

EXAMPLE I

Effect of SP and/or CP-96,345 on HIV Replication in MDM

Figure 1B:
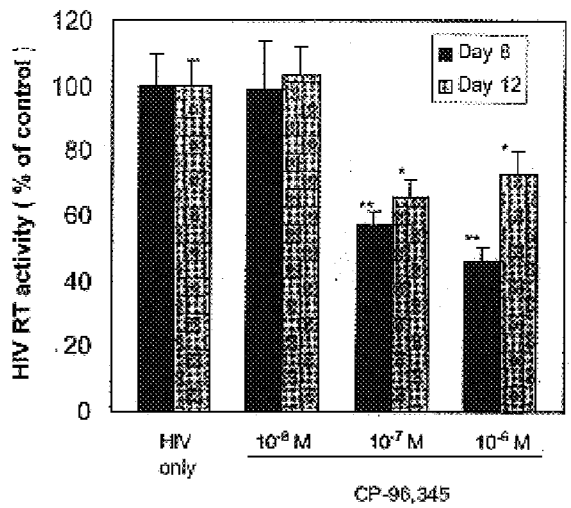
Figure 2A:
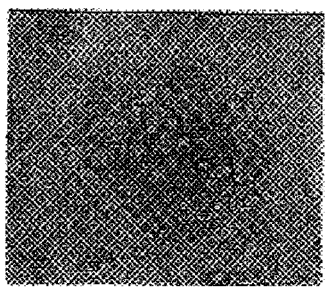
FIGS. 2A–2C. Effect of CP-96,345 on HIV-induced syncytium formation in MDM. The morphology of untreated and HIV-infected (2A), CP-96,345-treated ($10^{-7}$M) and infected (2B), and untreated and uninfected MDM (2C) was observed and photographed under a light microscope (X 400) 12 days after infection.
Figure 2B:
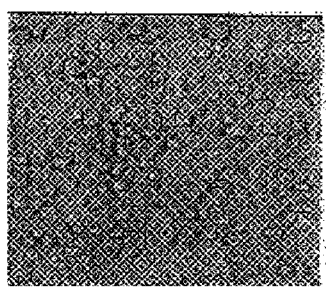
Figure 2C:
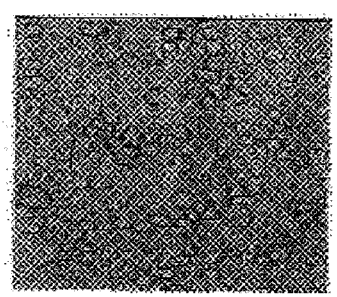

SP upregulated HIV replication in MDM in a concentration-dependent fashion (FIG. 1A), which is consistent with our previous observation (22). HIV RT activity was increased by 14% ($10^{-10}$M), 40% ($10^{-8}$M) and 58% ($10^{-6}$M), respectively (FIG. 1A). We thus determined whether the addition of CP-96,345 to MDM could inhibit HIV Bal strain infection of MDM. As shown in Fig. 1B, CP-96,345 inhibited HIV Bal strain infection of MDM in a concentration-dependent manner. The observed inhibition was 1% ($10^{-8}$M), 43% ($10^{-7}$M), and 54% ($10^{-6}$M), respectively on day 8 after HIV infection. HIV Bal strain-infected MDM cultures (without CP-96,345 treatment) demonstrated characteristic giant syncytia formation, whereas the SP antagonist-treated MDM failed to develop the giant syncytia induced by HIV Bal strain infection (FIG. 2).

Figure 3:
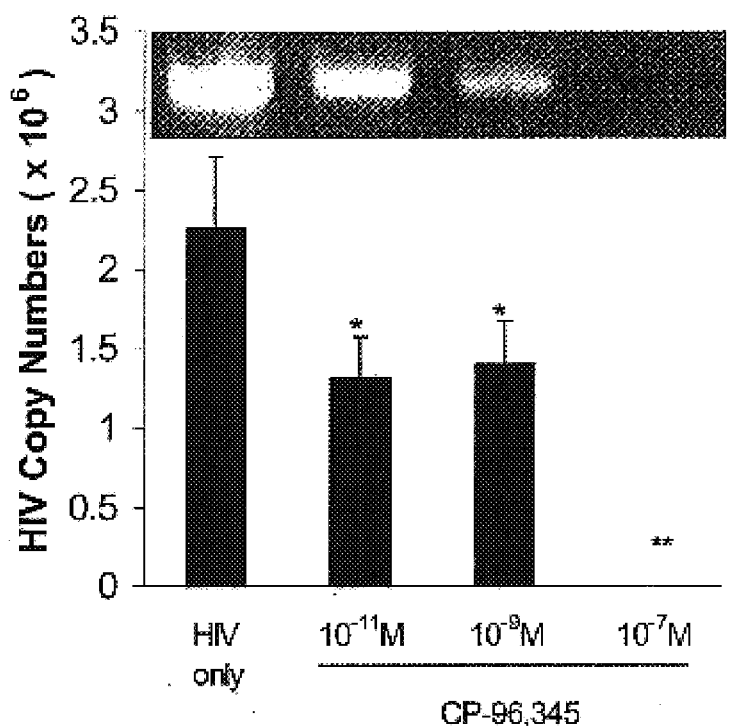
FIG. 3. Effect of CP-96,345 on the levels of HIV gag mRNA. The HIV Bal strain was used to infect MDM in the presence or absence of CP-96,345 ($10^{-11}$ to $10^{-7}$ M). HIV gag mRNA levels were determined by RT-PCR (top panel) using RNA extracted from the MDM 12 days after infection. β-Actin was used as the control to monitor the amount and integrity of RNA in each sample. HIV only: HIV Bal infected MDM as an infection control; MDM were infected with HIV Bal strain in the presence of CP-96,345 ($10^{-11}$M to $10^{-7}$M) as indicated; The graph shows data wherein HIV gag mRNA levels were quantified by real time RT-PCR using the same RNA samples as indicated in the top panel and the data are expressed as HIV gag mRNA copy numbers per PCR reaction. The data shown are presented as the mean±SD of triplicate cultures and are representative of three experiments (*$P<0.05$, **$P<0.01$, CP-96,345 vs HIV only).

In order to further examine the inhibition of CP-96,345 on HIV Bal strain at mRNA level, HIV gag gene expression was measured using RT-PCR. HIV gag mRNA expression was potently inhibited by CP-96,345 treatment in a concentration-dependent fashion (FIG. 3, top panel). In order to quantitatively measure mRNA copy numbers for HIV gag gene, we used real time RT-PCR to quantify the same samples shown in FIG. 3. Of note and most important to the findings reported here, CP-96,345 significantly suppress HIV gag gene mRNA expression at all three concentrations tested (See FIG. 3). CP-96,345 inhibited HIV replication by antagonism of NK-1R on MDM.

Figure 4:
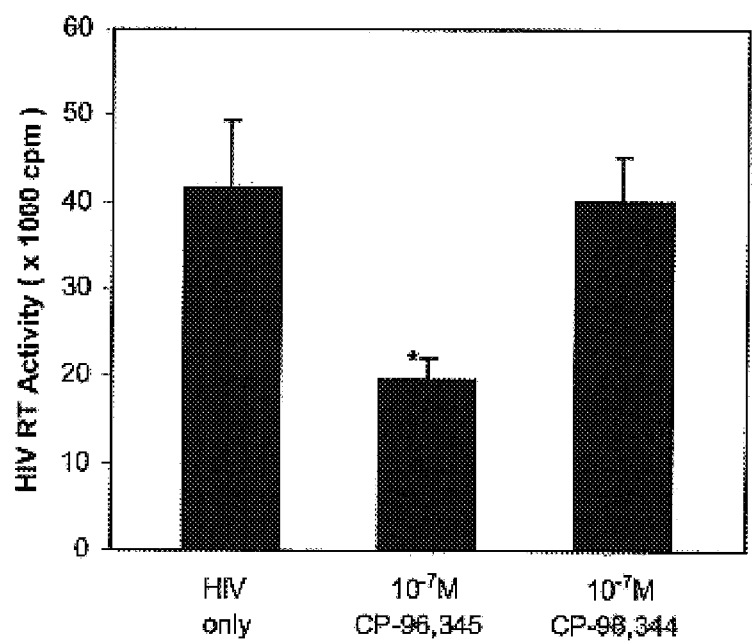
FIG. 4. Effect of CP-96,345 on HIV replication by antagonism of NK-1R on MDM. HIV Bal strain was used to infect MDM in the presence or absence of CP-96,345 ($10^{-7}$M), or CP-96,344 ($10^{-7}$M). HIV RT activity was determined in the culture supernatants collected 8 days after infection. RT activity in HIV-infected MDM was used as a positive control (HIV only), while that in HIV-infected MDM in the presence of CP-96,344 was used as a specificity control. The data shown are presented as the mean±SD of triplicate cultures and are representative of three experiments (*$P<0.05$, CP-96,345 vs HIV only).
Figure 5A:
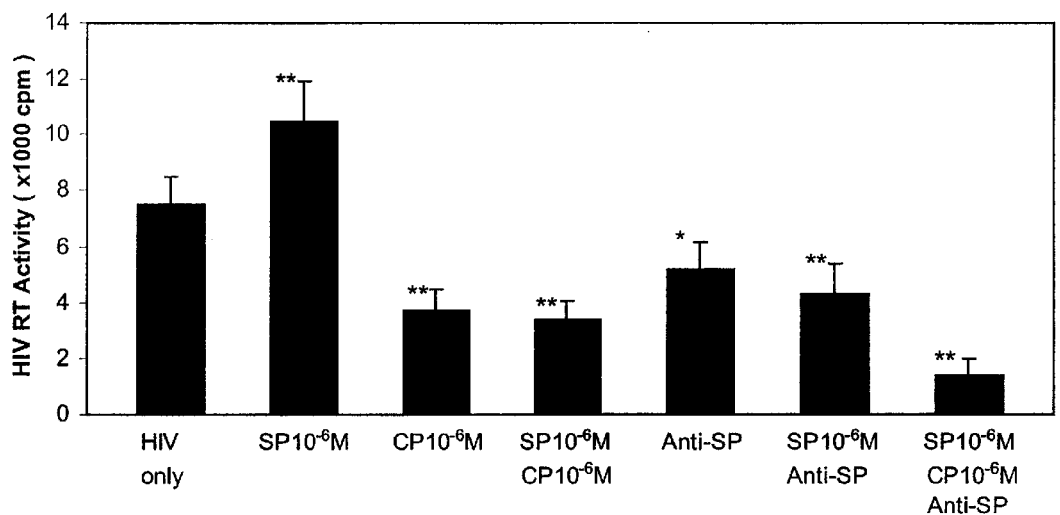
FIGS. 5A and 5B. Effect of CP-96,345 and/or anti-SP antibody on SP-enhanced HIV replication. HIV Bal strain was used to infect MDM in the presence or absence of SP ($10^{-6}$M) or CP-96,345 ($10^{-6}$M), or anti-SP antibody (1:1000 dilution) as indicated in the figure. CP: CP-96,345. HIV only: untreated and HIV Bal strain infected MDM was used as a control. HIV RT activity (5A) in the culture supernatants was determined 12 days after infection and HIV gag mRNA copy numbers (5B) were quantified using real-time RT-PCR 12 days after infection (5B). The data shown are presented as the mean±SD of triplicate cultures and are representative of three experiments (*$P<0.05$, **$P<0.01$, treatment vs HIV only).
Figure 5B:
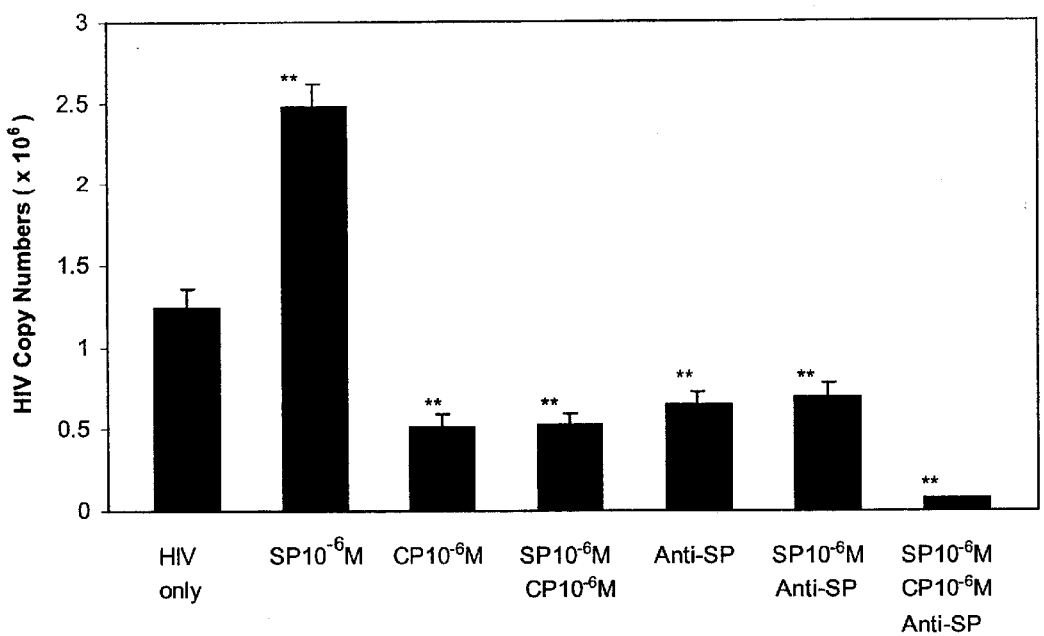

In order to determine whether inhibition of CP-96,345 on HIV infection of MDM is mediated by specific antagonism of NK-1R, MDM were incubated with CP-96,345 or its inactive enantiomer CP-96,344 for 2 h and then infected with HIV Bal strain. In comparison to the HIV infection control, viral replication was inhibited by CP-96,345 treatment ($10^{-7}$M), while CP-96,344 at the same concentration did not have the effect as determined by HIV RT activity (FIG. 4), demonstrating that CP-96,345 affected HIV replication through antagonism of NK-1R on MDM. In order to further test our hypothesis that SP-NK-1R interaction plays a role and is a necessary component in HIV replication in MDM, we incubated MDM with SP in the presence or absence of CP-96,345 or anti-SP antibody, or both for 2 h, and then infected the MDM with HIV Bal strain. As expected, SP alone enhanced HIV replication, while CP-96,345, anti-SP antibody and the combination of the both abrogated SP-enhanced HIV replication in MDM as determined by HIV RT activity and HIV gag mRNA levels (FIG. 5). Furthermore, treatment with CP-96,345 and/or anti-SP antibody down-regulated HIV replication to a level that was even lower than that of the HIV infection control (FIG. 5). The combination of anti-SP antibody and CP-96,345 had a synergistic effect on HIV replication in MDM, further demonstrating that both SP and SP receptors are involved in HIV infection of MDM and that interruption of SP autocrine loop resulted in inhibition of HIV replication in these cells (FIG. 5).

Effect of CP-96,345 on HIV Replication

Figure 6:
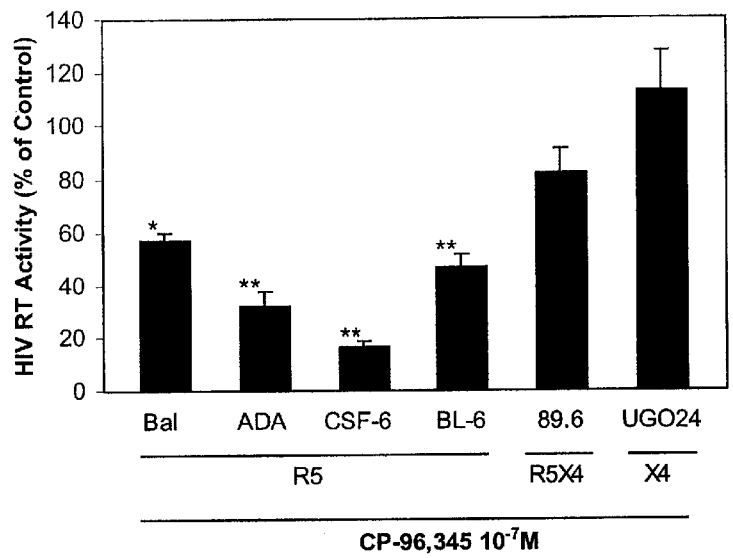
FIG. 6. Effect of CP-96,345 on HIV infection of MDM. Different HIV strains were used to infect MDM in the presence or absence of CP-96,345 ($10^{-7}$M). HIV RT activity in the culture supernatants was determined 8 days after infection. HIV RT activity in the CP-96,345-treated and HIV-infected MDM were expressed as percentage of that of untreated and HIV (corresponding strains)-infected MDM controls which were defined as 100%. The data shown are presented as the mean±SD of triplicate cultures and are representative of three experiments (*$P<0.05$, **$P<0.01$, CP-96,345 vs HIV only). R5: CCR5 tropic strains; X4: CXCR4 tropic strains; R5X4: dual tropic strains.

In order to determine the effect of CP-96,345 on different HIV tropic strains (R5, X4, and R5X4), MDM were incubated with or without CP-96,345 ($10^{-7}$M) and then infected with either R5 strains (Bal, ADA, CSF-6 and BL-6), or R5X4 strain (89.6), or X4 strain (UG024). In contrast to the prototype T cell line adapted X4 strains, UG024 is capable of using macrophage CXCR4 for infection (33), while 89.6 uses both macrophage CXCR4 and CCR5 (34). The replication of all R5 strains studied, including both prototype strains and primary isolates, was inhibited by CP-96,345 treatment, while the R5X4 strain (89.6) was inhibited to a lesser extent and the X4 strain (UG024) was not affected (FIG. 6).

Effect of SP on Activation of HIV LTR-Driven CAT Activity In U38 Cell Line

Figure 7:
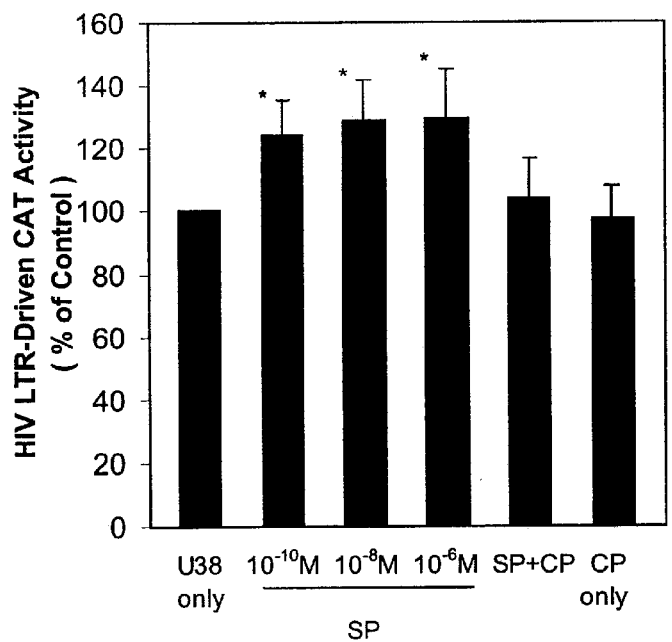
FIG. 7. Effect of SP on activation of HIV LTR-driven CAT activity in U38 cells. U38 cells were incubated with SP at different concentrations ($10^{-10}$ to $10^{-6}$M) or with CP-96,345 ($10^{-6}$M) and SP ($10^{-8}$ M) (SP+CP) or with CP-96,345 ($10^{-6}$M) alone (CP only) or untreated (U38 only) for 48 h. The untreated U38 cells were used as baseline control. The CAT activity (CPM) of the treated U38 cells was expressed as percentage of that of untreated baseline control cells. The data shown are presented as the mean±SD of triplicate cultures and are representative of three experiments (*$P<0.05$, SP treated U38 vs U38 only).

In order to determine whether SP activates HIV LTR promoter, we used U38 cells as a model for the experiments. SP significantly increased HIV LTR-driven CAT activity at the concentrations of $10^{-10}$ to $10^{-6}$M (P<0.05) in comparison to that of untreated control cells. This effect of SP ($10^{-8}$M) on HIV LTR was abrogated by CP-96,345 ($10^{-6}$M), indicating that SP activates HIV LTR through the interaction with NK-1R on the cell membrane (FIG. 7).

Effect of CP-96,345 on Macrophage Receptor Expression

Figure 8:
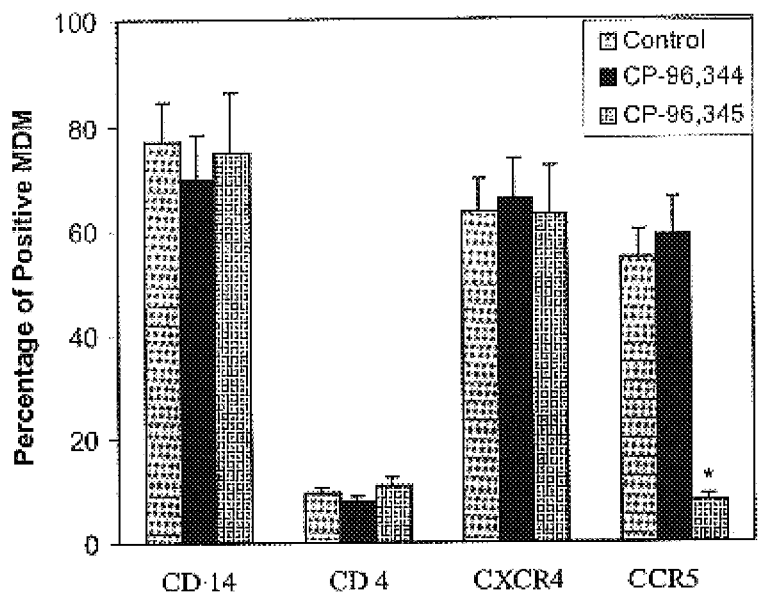
FIG. 8. Effect of CP-96,345 on macrophage receptor expression. MDM were incubated with or without CP-96,345 or CP-96,344 24 h and the MDM receptor expression was determined by direct immunofluorescence. The results shown are the percentage of MDM positive for the receptors analyzed, and are representative of three experiments. The data shown are presented as the mean±SD of triplicate cultures and are representative of three experiments (* $P<0.05$, CP-96,345 treated vs control).
Figure 9:
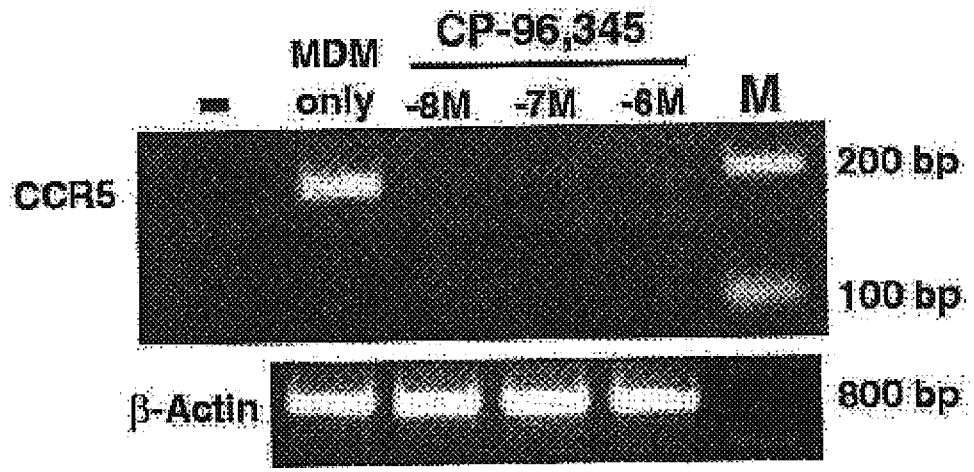
FIG. 9. Effect of CP-96,345 on CCR5 mRNA expression in MDM. (−): PCR negative control which represents lack of PCR products when reverse transcriptase was omitted from the RT reaction using RNA extracted from untreated MDM. MDM only: untreated MDM was used as a control. MDM were incubated with CP-96,345 ($10^{-8}$ to $10^{-6}$M) as indicated for 3 h and CCR5 mRNA was then amplified using RT-PCR. M: 100 base pair DNA ladder coelectrophoresed as markers. β-Actin was used to monitor the amount and integrity of RNA in each sample.

Since the replication of the HIV R5 strains but not the X4 strain was inhibited by CP-96,345, we hypothesized that SP-NK-1R interaction participated in the regulation of HIV coreceptor CCR5 expression. In order to examine the effect of CP-96,345 on HIV receptor expression, MDM were incubated overnight with or without CP-96,345 or CP-96, 344. Among the CD4, CCR5, CXCR4 and CD14 receptors, only CCR5 expression was down-regulated by CP-96,345, while CP-96,344 did not affect CCR5 receptor expression (FIG. 8). CCR5 mRNA was also down-regulated in MDM by CP-96,345 ($10^{-8}$ to $10^{-6}$M) (FIG. 9).

Effect of CP-96,345 on HIV Pseudotype Infection of MDM

Figure 10:
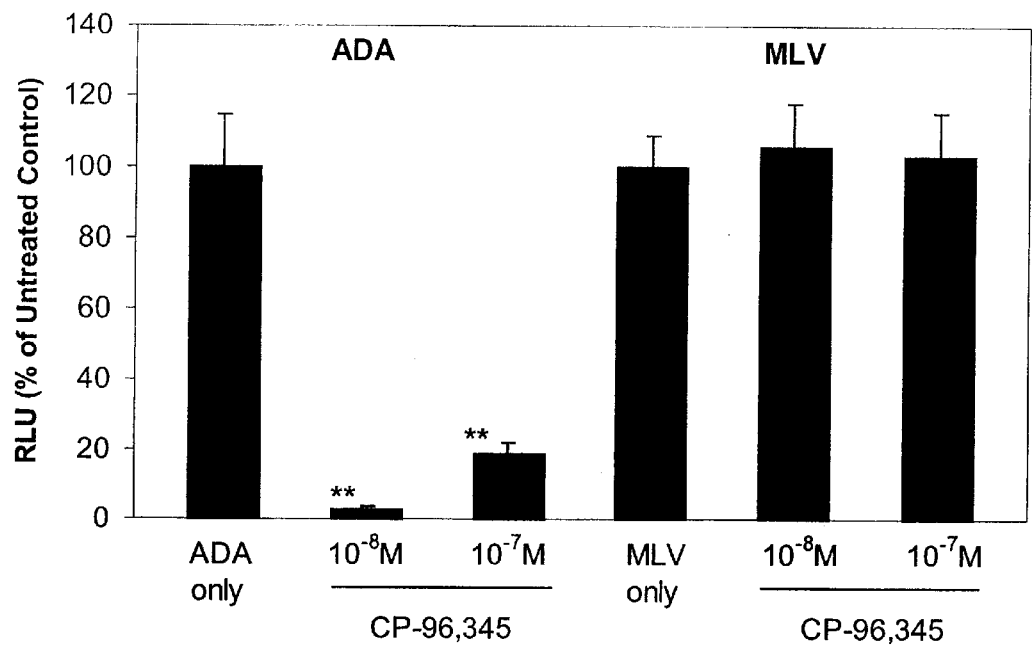
FIG. 10. Effect of CP-96,345 on pseudotyped HIV infection of MDM. Recombinant luciferase-encoding HIV reporter viruses pseudotyped with ADA Env or MLV Env were used to infect untreated MDM (ADA only or MLV only) and CP-96,345-pretreated MDM ($10^{-8}$ and $10^{-7}$ M overnight) as indicated. The data are expressed as relative RLU of CP-96,345-treated cells to that of untreated control (ADA only or MLV only) that is defined as 100%. The data shown are presented as the mean±SD of triplicate cultures and are representative of three experiments (** $P<0.01$, CP-96,345 treated vs ADA only).

In order to examine the functional relevance of CP-96, 345-mediated CCR5 down-regulation to HIV infection of MDM, the cells incubated with or without CP-96,345 were infected with luciferase-encoding HIV virions pseudotyped with either ADA Env (CCR5-dependent) or MLV Env (CCR5-independent). We observed that CP-96,345 inhibited M-tropic ADA infection of MDM as demonstrated by luciferase activity (FIG. 10). However, CP-96,345 failed to block MLV Env-pseudotyped HIV infection of MDM, indicating that the major effect of CP-96,345 inhibition is regulated by Env-determined early events in HIV entry into MDM.

Effect of CP-96,345 on TNF-A Synthesis in MDM

Figure 11:
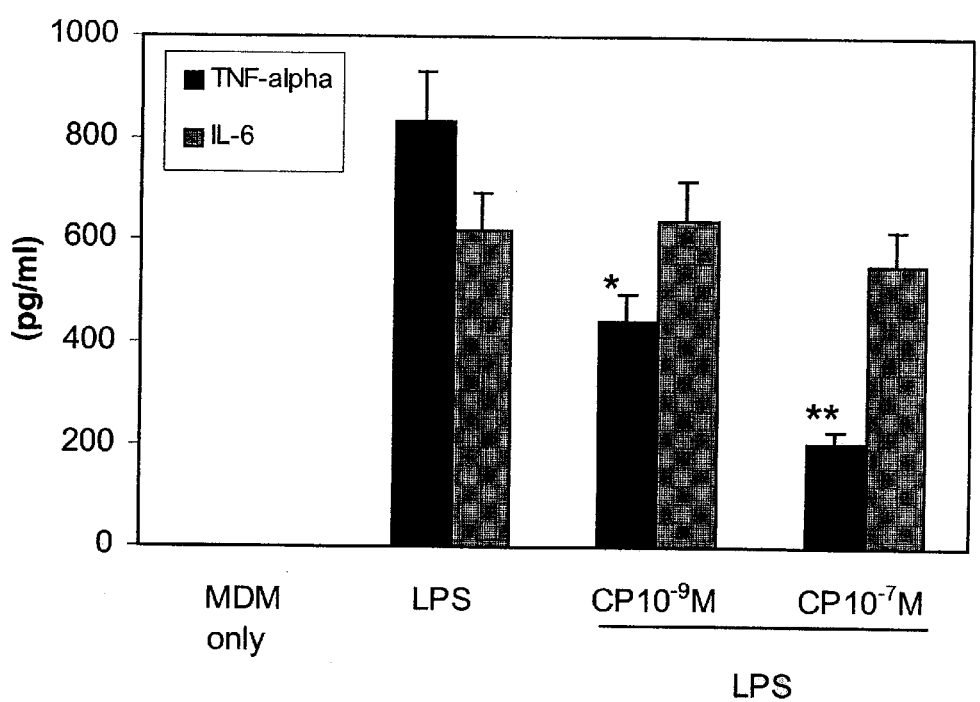
FIG. 11. Effect of CP-96,345 on cytokine production in MDM. MDM was incubated with or without CP-96,345 and/or LPS for 24 h. TNF-α and IL-6 levels in the culture supernatants were determined by ELISA. The treatment includes: untreated MDM (MDM only), MDM incubated with LPS (1 ng/ml) only (LPS); MDM incubated with LPS (1 ng/ml) plus CP-96,345 at the concentrations indicated. The data shown are presented as the mean±SD of triplicate cultures and are representative of three experiments (* $P<0.05$, **$P<0.01$, LPS and CP-96,345 treated vs LPS).

In order to determine whether SP participates in TNF-α synthesis in an autocrine fashion, the effect of CP-96,345 on LPS-stimulated TNF-A production in MDM was determined by ELISA. CP-96,345 attenuated LPS-stimulated TNF-A production in MDM in a concentration-dependent manner while IL-6 production was not affected (FIG. 11), indicating that the SP is involved in the regulation of TNF-α synthesis and secretion in an autocrine fashion.

EXAMPLE II

The potent effects of the cyclic amine CP-96,345 on HIV infection have been described in Example I. CP-96,345 is highly specific for the NK1 receptor. In the present example, the potent effects of a morpholino analog R-113281 are described. R-113281, a combined tachykinin receptor antagonist, has measurable binding affinity for all three neurokinin receptors, NK1, NK2, and NK3.

The methods utilized for the practice of Example II are essentially the same as those described in Example I.

Effect of R-113281 on HIV Infection of MDM

Figure 12:
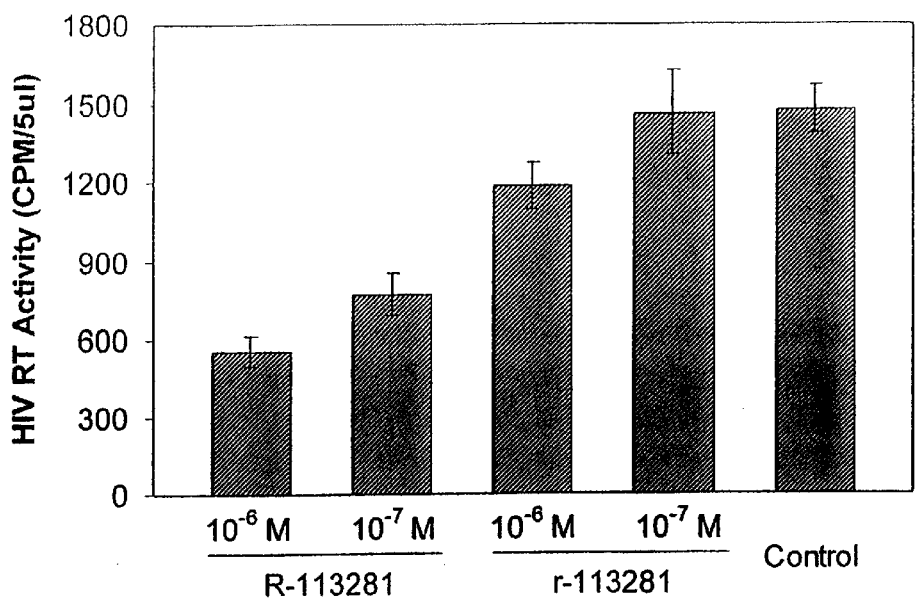
FIG. 12. A graph showing the effect of R113281 on HIV-1 infection of human peripheral blood MDM. Seven-day cultured MDM were treated with R113281 or r113281 (the inactive enantiomer of R-113281) for 2 hours and were then challenged with HIV-1M-tropic strain Bal for 2 hours in the presence or absence of the indicated concentrations of R113281 or r-113281. Supernatants were collected at day 8 post-infection for HIV-1 RT activity. The results are shown are mean±SD of triplicate cultures and representative of three experiments.

The effects of R113281 on HIV-1 infection of human peripheral blood MDM as assessed by RT activity were examined. Seven-day cultured MDM were treated with R113281 or r113281 (the inactive enantiomer of R-113281) for 2 hours and were then challenged with HIV-1M-tropic strain Bal for 2 hours in the presence or absence of the indicated concentrations of R113281 or r-113281. Supernatants were collected at day 8 post-infection for HIV-1 RT activity. FIG. 12 reveals that administration of R-113281, but not its inactive enantiomer significantly reduced HIV RT activity.

Figure 13:
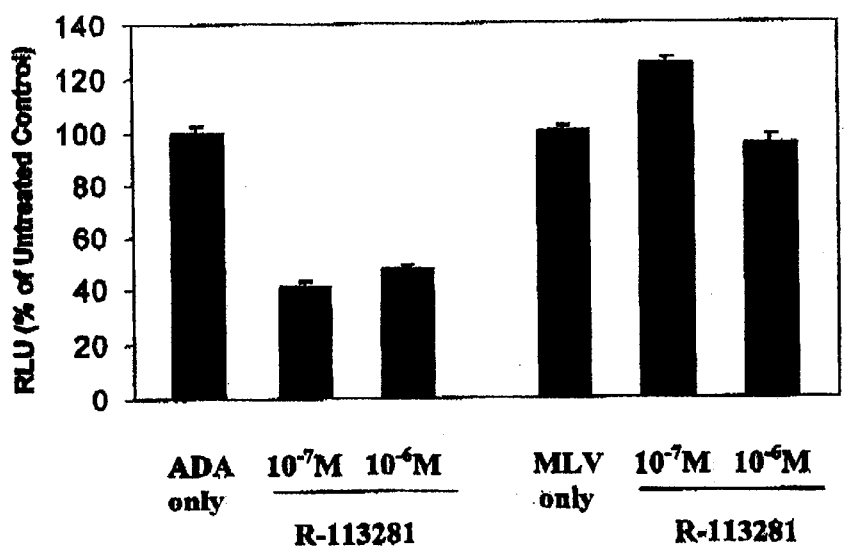
FIG. 13. A graph showing the effect of R113281 on pseudotyped HIV infection of MDM. Recombinant luciferase-encoding HIV reporter viruspseudotyped with ADA (M-tropic) Env or MLV Env (HIV-receptor inductance) were used to infect untreated MDM (ADA only or MLV only and R-113281 pretreated MDM ($10^{-7}$ and $10^{-6}$ overnight as indicated. The data are expressed as relative light unit (RLU) of R-113281-treated cells to that of untreated control (ADA only or MLV only) that is defined as 100%, FIG. 14. A graph showing the effect of R-113281 ($10^{-6}$ M) on different strains of HIV. HIV RT activity in the culture supernatants was determined 8 days after infection. HIV RT activity in the R-113281-treated and HIV-infected MDM were expressed as a percentage of that of untreated and HIV (corresponding strain)-infected MDM controls which were defined as 100%. R5:CCR5 tropic strains; X4: CXCR4 tropic strains and R5X4: dual tropic strains.

The effect of R113281 on pseudotyped HIV infection of MDM was determined. Recombinant luciferase-encoding HIV reporter virus pseudotyped with ADA (M-tropic) Env or MLV Env (HIV-receptor inductance) were used to infect untreated MDM (ADA only or MLV only and R-113281 pretreated MDM ($10^{-7}$ and $10^{-6}$ overnight as indicated. The data are expressed as relative light unit (RLU) of R-113281-treated cells to that of untreated control (ADA only or MLV only) that is defined as 100%. As observed with CP-96,345, the data showed that R-113281 inhibited M-tropic ADA infection of MDM as demonstrated by luciferase activity (FIG. 13). However, R-113281 failed to block MLV-Env pseudotyped HIV infection of MDM, indicating that the major effect of R-113281 inhibition is regulated by Env-determined early events in HIV entry into MDM.

Figure 14:
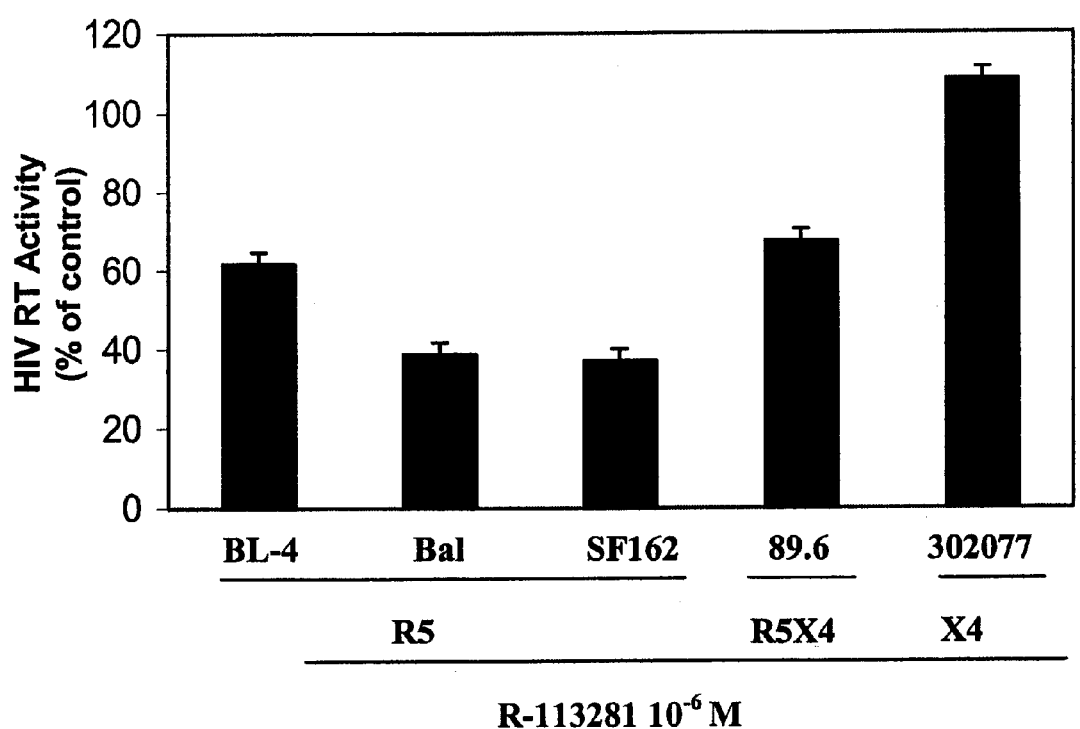

The inhibitory effects of R-113281 ($10^{-6}$ M) on different HIV tropic strains (R5, X4 and R5X4) of HIV were also assessed. HIV RT activity in the culture supernatants was determined 8 days after infection. HIV RT activity in the R-113281-treated and HIV-infected MDM were expressed as a percentage of that of untreated and HIV (corresponding strain)-infected MDM controls which were defined as 100%. R5:CCR5 tropic strains; X4:CXCR4 tropic strains and R5X4: dual tropic strains. The replication of all R5 strains was inhibited by R-113281 treatment, while the R5X4 strain was inhibited to a lesser extent and the X4 strain was not affected. See FIG. 14.

EXAMPLE III

Combined Administration Of NK Receptor Antagonists For The Treatment Of HIV Infection CCR5 is believed to play an important role in HIV entry in the macrophage. MDM were incubated with CP-96,345 ($10^{-7}$ M to $10^{-6}$ M) or R-113281 ($10^{-8}$ M to $10^{-6}$ M) as indicated for 4 hours. Relative CCR5 mRNA level was quantified by a real-time RT-PCR assay. Untreated MDM was used a control. The inhibitory effects of CP-96,345 and R-113281 on CCR5 expression are shown in FIGS. 8, 9, 15A and 15B. The data reveal that both the sole and combined NK receptor antagonists significantly down-regulated CCR5 expression at the mRNA level. FIG. 15B shows that R-113281 also inhibited CCR5 protein expression.

Figure 16:
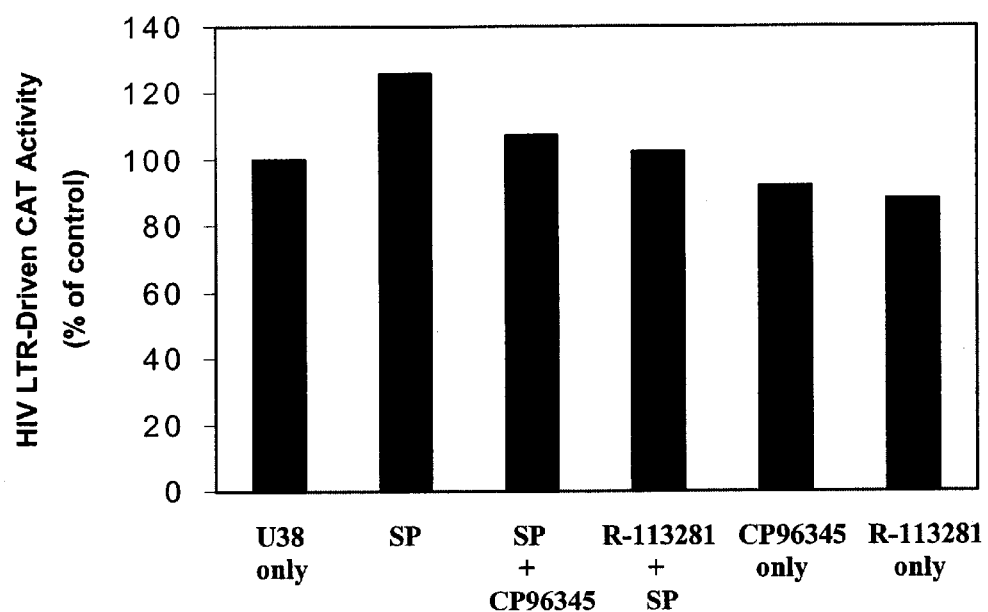
FIG. 16. A graph showing the effect of SP on activation of HIV LTR-driven CAT activity in U38 cells. U38 cells were incubated with or without the reagents for 48 hours. SP ($10^{-5}$M) CP-96,345 ($10^{-6}$M) and R-113281 ($10^{-6}$M) The untreated U38 cells were used as a baseline control. The CAT activity (CPM) of the treated and untreated U38 cells was expressed as a percentage of that of untreated baseline control cells.

The effect of SP on activation of HIV LTR-driven CAT activity in U38 cells was determined. U38 cells were incubated with or without the reagents for 48 hours. SP ($10^{-5}$M) CP-96,345 ($10^{-6}$M) and R-113281 ($10^{-6}$M) were administered at the indicated concentrations. The untreated U38 cells were used as a baseline control. As shown in FIG. 16, SP significantly increases HIV LRT-driven CAT activity. This effect of SP ($10^{-8}$M) was abrogated by R-113281 indicating that SP activates the HIV LTR through interaction with NK receptors on the cell membrane.

Figure 17:
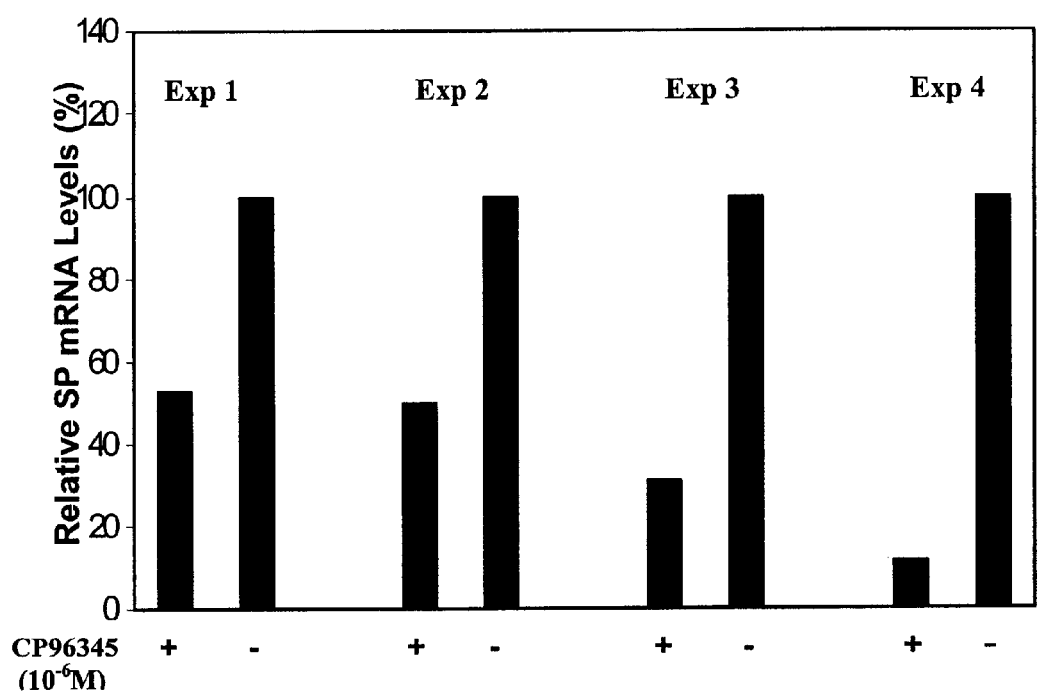
FIG. 17. A graph showing the effect of CP-96,345 on SP mRNA expression in MDM. The MDM were incubated with (+) or without (−) the NK-1R antagonist at the indicated concentration for 4 hours. The SP mRNA levels were determined by a real-time RT-PCR. The SP mRNA levels in the CP-96,345 treated MDM are expressed as a percentage of that in untreated MDM which are defined as 100%.

The effect of CP-96,345 on SP mRNA expression in MDM was also determined. The MDM were incubated with (+) or without (−) the NK-1R antagonist at the indicated concentration for 4 hours. The SP mRNA levels were determined by a real-time RT-PCR. The data show that CP-96,345 significantly inhibited expression of SP mRNA in MDM. See FIG. 17.

Figure 18:
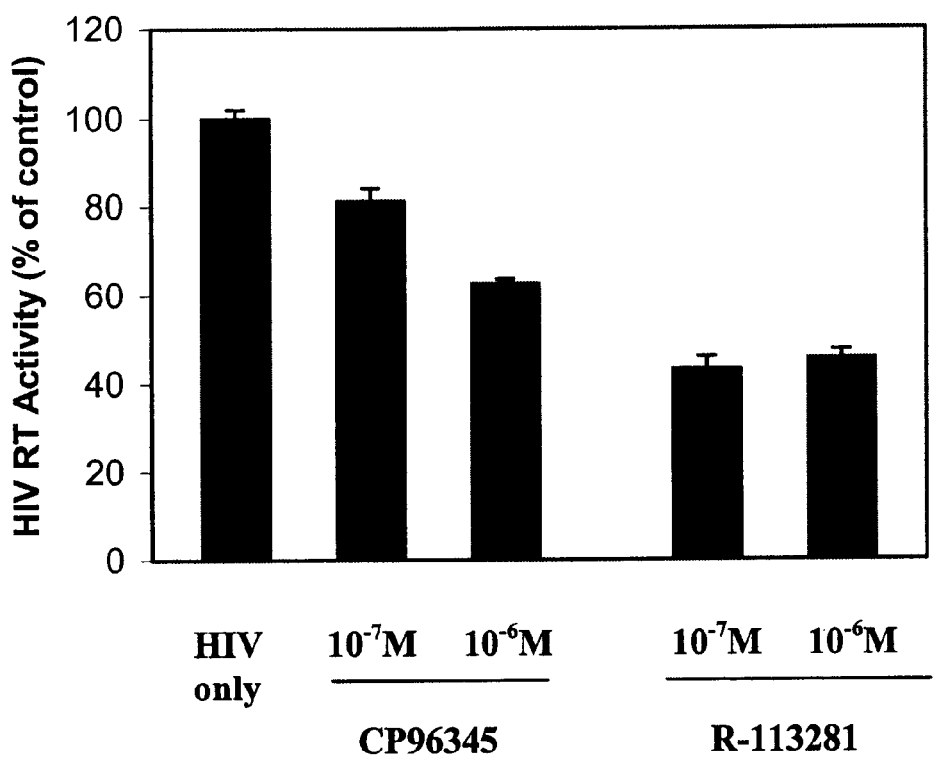
FIG. 18. A graph showing the effects of CP-96,345 and R-113281 ($10^{-7}$–$10^{-6}$M) on HIV infection of MDM. The HIV Bal strain was used to infect MDM in the presence or absence of the above-identified NK1 receptor antagonists. HIV RT activity was measured as described above.

The inhibitory effects of CP-96,345 and R-113281 ($10^{-7}$–$10^{-6}$M) on RT activity during HIV infection of MDM are shown in FIG. 18. The HIV Bal strain was used to infect MDM in the presence or absence of the above-identified NK receptor antagonists. Inasmuch as CP-96,345 and R-113281 interact with NK receptors at different sites, methods for administration of both compounds simultaneously are with the scope of the present invention. It is anticipated that such combined, simultaneous administration of the two NK receptor antagonists would act synergistically to inhibit HIV entry into MDM. Such therapeutic combinations may include administration of additional anti-retroviral agents, such as protease inhibitors and DNA polymerase inhibitors. Moreover, the NK antagonists of the invention may be administered in conjunction with AIDS specific vaccines.

In accordance with the present invention, we have demonstrated that the SP antagonist, CP-96,345, and the NK1, NK2, NK3 combined neurokinin receptor antagonist, R-113281, potently inhibited HIV (R5 strains) replication in human peripheral blood MDM. Since SP is involved in the modulation of HIV infection of MDM and there is an autocrine regulation of SP, the observed inhibition is the consequence of the interruption of SP autocrine loop through antagonism of SP-NK-1R interaction on the cell membrane. The following data strongly support this hypothesis: 1) both CP-96,345 and anti-SP antibody inhibited SP-enhanced HIV Bal strain replication in MDM; 2) CP-96,345 inhibited HIV R5 strain replication in MDM, while its inactive enantiomer, CP-96,344 was ineffective; 3) the HIV R5 (CCR5 dependent) strain replication was inhibited, while the R5X4 dual tropic strain (89.6) and the X4 (UG024) strain were partially inhibited or not affected, respectively.

Furthermore, we observed that CP-96,345 down-regulated CCR5 expression in MDM, while CP-96,344, the inactive enantiomer of CP-96,345 was ineffective (FIG. 8 and FIG. 9). R-113281 also down-regulated CCR5 expression. Down-regulation of CCR5 is functionally relevant to the decreased susceptibility to HIV infection by MDM. This observation is further supported by the findings that both R-113281 and CP-96,345 inhibited the replication of HIV R5 strains but not the X4 strain and that only ADA Env-pseudotyped HIV infection was inhibited. These data strongly indicate that SP autocrine loop is involved in the regulation of CCR5 expression in MDM and that down-regulation of CCR5 expression on MDM by CP-96,345 and R-113281 is due to an interruption of this autocrine loop in these cells. Recent studies have demonstrated that TNF-α up-regulates CCR5 expression in macrophages (41) and PBMC (42) and altered HIV expression in monocytes in vitro (6, 7). Thus, CP-96,345-mediated TNF-α regulation may be partially responsible for the down-regulation of CCR5 expression in MDM.

Taken together, these in vitro effects of the NK antagonist CP-96,345 and R-113281, including down-regulation of CCR5 receptor expression on MDM, and inhibition of HIV R5 strain replication in MDM, offer approaches to the design of new anti-HIV therapeutics.

REFERENCES

1. Marriott, I., Mason, M. J., Elhofy, A. & Bost, K. L. (2000) *J. Neuroimmunol.* 102, 163–71.
2. Lieb, K., Fiebich, B. L., Berger, M., Bauer, J. & Schulze-Osthoff, K. (1997) *J. Immunol.* 159, 4952–8.
3. Lotz, M., Vaughan, J. H. & Carson, D. A. (1988) *Science* 241, 1218–21.
4. Laurenzi, M. A., Persson, M. A., Dalsgaard, C. J. & Haegerstrand, A. (1990) *Scand. J. Immunol.* 31, 529–33.
5. Kincy-Cain, T. & Bost, K. L. (1997) *J. Immunol.* 158, 2334–9.
6. Rosenberg, Z. F. & Fauci, A. S. (1990) *Immunol. Today* 11, 176–80.
7. Rosenberg, Z. F. & Fauci, A. S. (1991) *FASEB J.* 5, 2382–90.
8. Pascual, D. W. & Bost, K. L. (1990) *Immunology* 71, 52–6.
9. Castagliuolo, I., Keates, A. C., Qiu, B., Kelly, C. P., Nikulasson, S., Leeman, S. E. & Pothoulakis, C. (1997) *Proc. Natl. Acad. Sci. U. S. A.* 94, 4788–93.
10. Cioni, C., Renzi, D., Calabro, A. & Annunziata, P. (1998) *J. Neuroimmunol.* 84, 76–85.
11. Bae, S., Matsunaga, Y., Tanaka, Y. & Katayama, I. (1999) *Biochemical & Biophysical Research Communications* 263, 327–33.
12. Toneatto, S., Finco, O., van der Putten, H., Abrignani, S. & Annunziata, P. (1999) *AIDS* 13, 2343–8.
13. Lucey, D. R., Novak, J. M., Polonis, V. R., Liu, Y. & Gartner, S. (1994) *Clinical & Diagnostic Laboratory Immunology* 1, 330–5.
14. Bost, K. L., Breeding, S. A. & Pascual, D. W. (1992) *Reg. Immunol.* 4, 105–12.
15. De Giorgio, R., Tazzari, P. L., Barbara., Stanghellini, V. & Corinaldesi, R. (1998) *J. Neuroimmunol.* 82, 175–81.
16. Ho, W. Z., Lai, J. P., Zhu, X. H., Uvaydova, M. & Douglas, S. D. (1997) *J. Immunol.* 159, 5654–60.
17. Lai, J. P., Douglas, S. D., Rappaport, E., Wu, J. M. & Ho, W. Z. (1998) *J. Neuroimmunol.* 91, 121–8.
18. Lai, J. P., Douglas, S. D. & Ho, W. Z. (1998) *J. Neuroimmunol.* 86, 80–6.
19. Castagliuolo, I., Riegler, M., Pasha, A., Nikulasson, S., Lu, B., Gerard, C., Gerard, N. P. & Pothoulakis, C. (1998) *J. Clin. Invest.* 101, 1547–50.
20. Azzari, C., Rossi, M. E., Resti, M., Caldini, A. L., Lega, L., Galli, L., Fico, E. & Vierucci, A. (1992) *Pediatr. Med. Chir.* 14, 577–81.
21. Annunziata, P., Cioni, C., Toneatto, S. & Paccagnini, E. (1998) *AIDS* 12, 2377–85.
22. Ho, W. Z., Cnaan, A., Li, Y. H., Zhao, H., Lee, H. R., Song, L. & Douglas, S. D. (1996) *AIDS Research & Human Retroviruses* 12, 195–8.
23. Hassan, N. F., Campbell, D. E. & Douglas, S. D. (1986) *J. Immunol. Methods* 95, 273–6.
24. Hassan, N. F., Cutilli, J. R. & Douglas, S. D. (1990) *J. Immunol. Methods* 130, 283–5.
25. Clouse, K. A., Powell, D., Washington, I., Poli, G., Strebel, K., Farrar, W., Barstad, P., Kovacs, J., Fauci, A. S. & Folks, T. M. (1989) *J. Immunol.* 142, 431–8.
26. Felber, B. K. & Pavlakis, G. N. (1988) *Science* 239, 184–7.
27. Collin, M. & Gordon, S. (1994) *Virology* 200, 114–20.
28. Snider, R. M., Constantine, J. W., Lowe, J. A. d., Longo, K. P., Lebel, W. S., Woody, H. A., Drozda, S. E., Desai, M. C., Vinick, F. J., Spencer, R. W. & et al. (1991) *Science* 251, 435–7.

29. Berger, E. A., Doms, R. W., Fenyo, E. M., Korber, B. T., Littman, D. R., Moore, J. P., Sattentau, Q. J., Schuitemaker, H., Sodroski, J. & Weiss, R. A. (1998) *Nature* 391, 240.
30. Willey, R. L., Smith, D. H., Lasky, L. A., Theodore, T. S., Earl, P. L., Moss, B., Capon, D. J. & Martin, M. A. (1988) *Journal of Virology* 62, 139–47.
31. Connor, R. I., Chen, B. K., Choe, S. & Landau, N. R. (1995) *Virology* 206, 935–44.
32. Huang, Y., Paxton, W. A., Wolinsky, S. M., Neumann, A. U., Zhang, L., He, T., Kang, S., Ceradini, D., Jin, z., Yazdanbakhsh, K., Kunstman, K., Erickson, D., Dragon, E., Landau, N. R., Phair, J., Ho, D. D. & Koup, R. A. (1996) *Nat. Med.* 2, 1240–3.
33. Yi, Y., Isaacs, S. N., Williams, D. A., Frank, I., Schols, D., De Clercq, E., Kolson, D. L. & Collman, R. G. (1999) *Journal of Virology* 73, 7117–25.
34. Yi, Y., Rana, S., Turner, J. D., Gaddis, N. & Collman, R. G. (1998) *Journal of Virology* 72, 772–7.
35. Quinlan, K. L., Naik, S. M., Cannon, G., Armstrong, C. A., Bunnett, N. W., Ansel, J. C. & Caughman, S. W. (1999) *J. Immunol.* 163, 5656–65.
36. Liu, R., Zhao, X., Gurney, T. A. & Landau, N. R. (1998) *AIDS Research & Human Retroviruses* 14, 1509–19.
37. Ho, W. Z., Kaufman, D., Uvaydova, M. & Douglas, S. D. (1996) *J. Neuroimmunol.* 71, 73–80.
38. Ho, W. Z., Stavropoulos, G., Lai, J. P., Hu, B. F., Magafa, V., Anagnostides, S. & Douglas, S. D. (1998) *J. Neuroimmunol.* 82, 126–32.
39. Dickerson, C., Undem, B., Bullock, B. & Winchurch, R. A. (1998) *J. Leukoc. Biol.* 63, 602–5.
40. Lee, H. R., Ho, W. Z. & Douglas, S. D. (1994) *Clinical & Diagnostic Laboratory Immunology* 1, 419–23.
41. Wahl, S. M., Greenwell-Wild, T., Peng, G., Hale-Donze, H., Doherty, T. M., Mizel, D. & Orenstein, J. M. (1998) *Proc. Natl. Acad. Sci. U. S. A.* 95, 12574–9.
42. Patterson, B. K., Czerniewski, M., Andersson, J., Sullivan, Y., Su, F., Jiyamapa, D., Burki, Z. & Landay, A. (1999) *Clin. Immunol.* 91, 254–62.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method f or inhibiting HIV infection in a patient in need thereof comprising the administration of at least one antagonist specific for the neurokinin receptor family in an effective amount to said patient.

2. The method of claim 1, wherein said at least one antagonist has specific binding affinity for the NK1 receptor.

3. The method of claim 2, wherein said antagonist is CP-96,345.

4. The method of claim 1, wherein said antagonist is a combined antagonist and has binding affinity for the NK1, NK2 and NK3 receptors.

5. The method of claim 4, wherein said antagonist is R-113281.

6. The method of claim 1, wherein said at least one antagonist comprises both CP-96,345 and R-113281.

7. The method of claim 1, wherein said antagonist is administered to said patient via a route selected from the group consisting of intravenous administration, topical administration, parenteral administration and oral administration.

8. The method of claim 1, wherein said at least one antagonist is administered in combination with at least one additional anti-retroviral agents.

9. A method f or inhibiting HIV infection of a monocyte derived macrophage, comprising contacting said macrophage with at least one NK receptor antagonist.

10. The method of claim 9, wherein said at least one antagonist has specific binding affinity for the NK1 receptor.

11. The method of claim 10, wherein said antagonist is CP-96,345.

12. The method of claim 9, wherein said antagonist is a combined antagonist and has binding affinity for the NK1, NK2 and NK3 receptors.

13. The method of claim 12, wherein said antagonist is R-113281.

14. The method of claim 9, wherein said at least one antagonist comprises both CP-96,345 and R-113281.

15. The method of claim 9, wherein said at least one antagonist is administered in combination with at least one other anti-retroviral agent.

* * * * *

```
                              SEQUENCE LISTING

<160> NUMBER OF SEQ ID NOS: 5

<210> SEQ ID NO 1
<211> LENGTH: 23
<212> TYPE: DNA
<213> ORGANISM: Artificial Sequence
<220> FEATURE:
<223> OTHER INFORMATION: Primer

<400> SEQUENCE: 1
tgacatgctg tcatcatttc ttc                                           23

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
cctgtgcctc ttcttctcat ttcg                                          24

<210> SEQ ID NO 3
<211> LENGTH: 28
<212> TYPE: DNA
<213> ORGANISM: Artificial Sequence
<220> FEATURE:
<223> OTHER INFORMATION: Primer

<400> SEQUENCE: 3
ataatccacc tatcccagta ggagaaat                                      28

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
```

-continued tttggtcctg tcttatgtcc agaatgc                                    27

<210> SEQ ID NO 5
<211> LENGTH: 42
<212> TYPE: DNA
<213> ORGANISM: Artificial Sequence
<220> FEATURE:
<223> OTHER INFORMATION: Probe

<400> SEQUENCE: 5
atcctgggga ttaaataaaa tagtaagaat gtatagccct ac                   42